United States Patent
Ukegawa et al.

(10) Patent No.: US 12,171,645 B2
(45) Date of Patent: Dec. 24, 2024

(54) AUXILIARY ABSORBENT ARTICLE

(71) Applicant: LIVEDO CORPORATION, Ehime (JP)

(72) Inventors: Kazuo Ukegawa, Tokushima (JP); Rei Ito, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 392 days.

(21) Appl. No.: 17/618,755

(22) PCT Filed: Apr. 21, 2020

(86) PCT No.: PCT/JP2020/017186
§ 371 (c)(1),
(2) Date: Dec. 13, 2021

(87) PCT Pub. No.: WO2020/255554
PCT Pub. Date: Dec. 24, 2020

(65) Prior Publication Data
US 2022/0313505 A1 Oct. 6, 2022

(30) Foreign Application Priority Data
Jun. 21, 2019 (JP) ................................. 2019-115623

(51) Int. Cl.
*A61F 13/70* (2006.01)
*A61F 13/49* (2006.01)

(52) U.S. Cl.
CPC .......... *A61F 13/70* (2013.01); *A61F 13/4906* (2013.01)

(58) Field of Classification Search
CPC ............... A61F 13/4755; A61F 13/505; A61F 13/5611; A61F 13/60; A61F 13/66;
(Continued)

(56) References Cited

U.S. PATENT DOCUMENTS 2,838,048 A * 6/1958 Kowalski ............ A61F 13/5611
604/387
3,044,467 A * 7/1962 Campau ................ A61F 13/472
2/46
(Continued)

FOREIGN PATENT DOCUMENTS

CN 106618873 5/2017
JP 55-75317 5/1980
(Continued)

OTHER PUBLICATIONS

Decision of Refusal issued Oct. 18, 2023 in corresponding Japanese Patent Application No. 2019-115623, with English language translation.

(Continued)

*Primary Examiner* — Catharine L Anderson
(74) *Attorney, Agent, or Firm* — Wenderoth, Lind & Ponack, L.L.P.

(57) ABSTRACT

An auxiliary absorbent article is for attachment to a skin facing side of another absorbent article, and has a longitudinal direction and a width direction. The auxiliary absorbent article includes: (i) a main body including an absorber and a liquid-permeable cover sheet which covers an inner facing side of the absorber and an outer facing side of the absorber; (ii) an adhesive part on an outer facing side of the main body; and (iii) a release sheet on an outer facing side of the adhesive part to cover the adhesive part. The release sheet extends outward in the longitudinal direction beyond an end edge of the main body.

9 Claims, 5 Drawing Sheets

(58) Field of Classification Search
CPC ........ A61F 13/665; A61F 13/68; A61F 13/70; A61F 13/74; A61F 13/76; A61F 2013/5055; A61F 2013/5683
See application file for complete search history.

(56) References Cited

U.S. PATENT DOCUMENTS

| | | | | |
|---|---|---|---|---|
| 4,770,657 | A | * | 9/1988 | Ellis .................... A61F 13/4752 604/385.101 |
| 4,804,380 | A | * | 2/1989 | Lassen .............. A61F 13/47227 604/378 |
| 4,917,675 | A | * | 4/1990 | Taylor ................ A61F 13/5514 604/385.03 |
| 6,783,519 | B2 | * | 8/2004 | Samuelsson ........ A61F 13/5611 604/385.05 |
| 6,793,649 | B1 | | 9/2004 | Fujioka et al. |
| 6,936,038 | B2 | * | 8/2005 | Tears ................... A61F 13/505 604/385.04 |
| 2002/0143316 | A1 | | 10/2002 | Sherrod et al. |
| 2007/0197991 | A1 | * | 8/2007 | Wetter ............. A61F 13/15723 604/385.03 |

FOREIGN PATENT DOCUMENTS

| | | |
|---|---|---|
| JP | 58-18520 | 2/1983 |
| JP | 1-69521 | 5/1989 |
| JP | 11-267145 | 10/1999 |
| JP | 2004-89270 | 3/2004 |
| JP | 2004-261442 | 9/2004 |
| JP | 2007-75137 | 3/2007 |
| JP | 2009-189380 | 8/2009 |
| JP | 2010-131087 | 6/2010 |
| JP | 2011-72612 | 4/2011 |

OTHER PUBLICATIONS

International Search Report issued Jul. 14, 2020 in International (PCT) Application No. PCT/JP2020/017186.
Japanese Office Action issued Jan. 31, 2023 in corresponding Japanese Patent Application No. 2019-115623, with English machine translation.
Office Action issued Apr. 16, 2024 in Japanese Patent Application No. 2023-172916, with English translation.
Office Action dated Sep. 10, 2024 in Japanese Patent Application No. 2023-172916, with Machine Translation.

* cited by examiner

[Fig. 1]
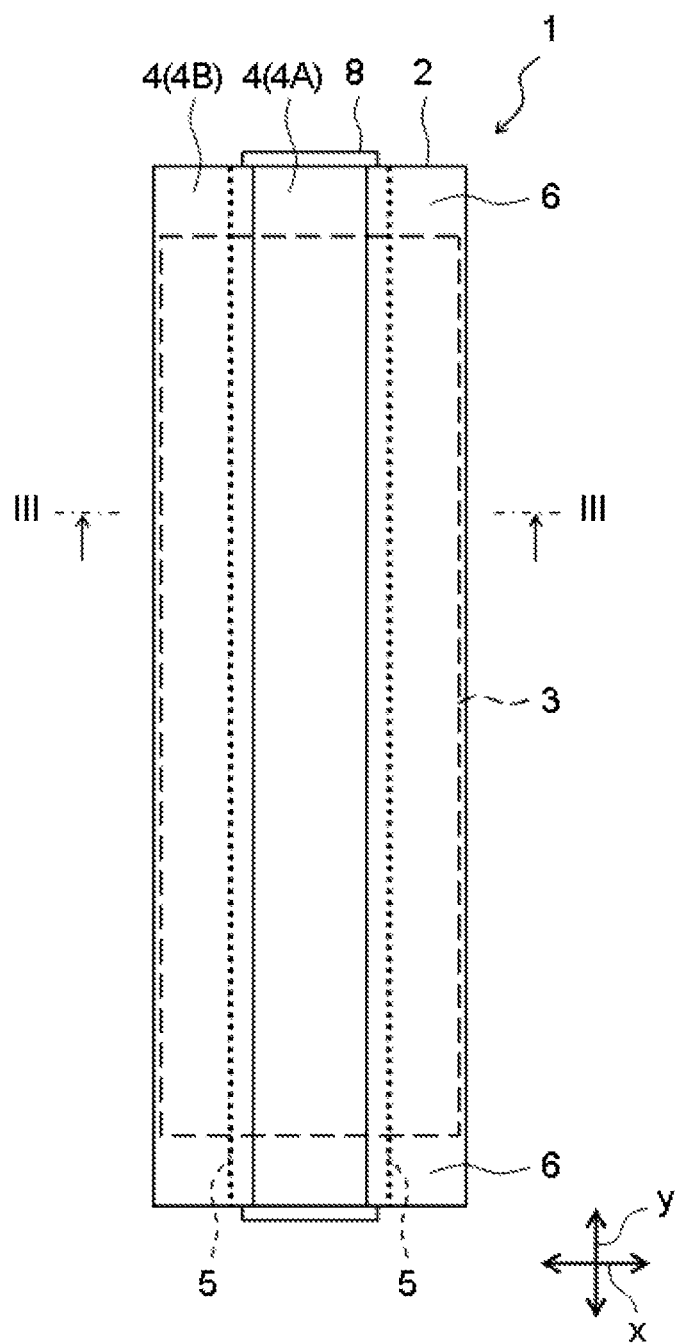

[Fig. 2]
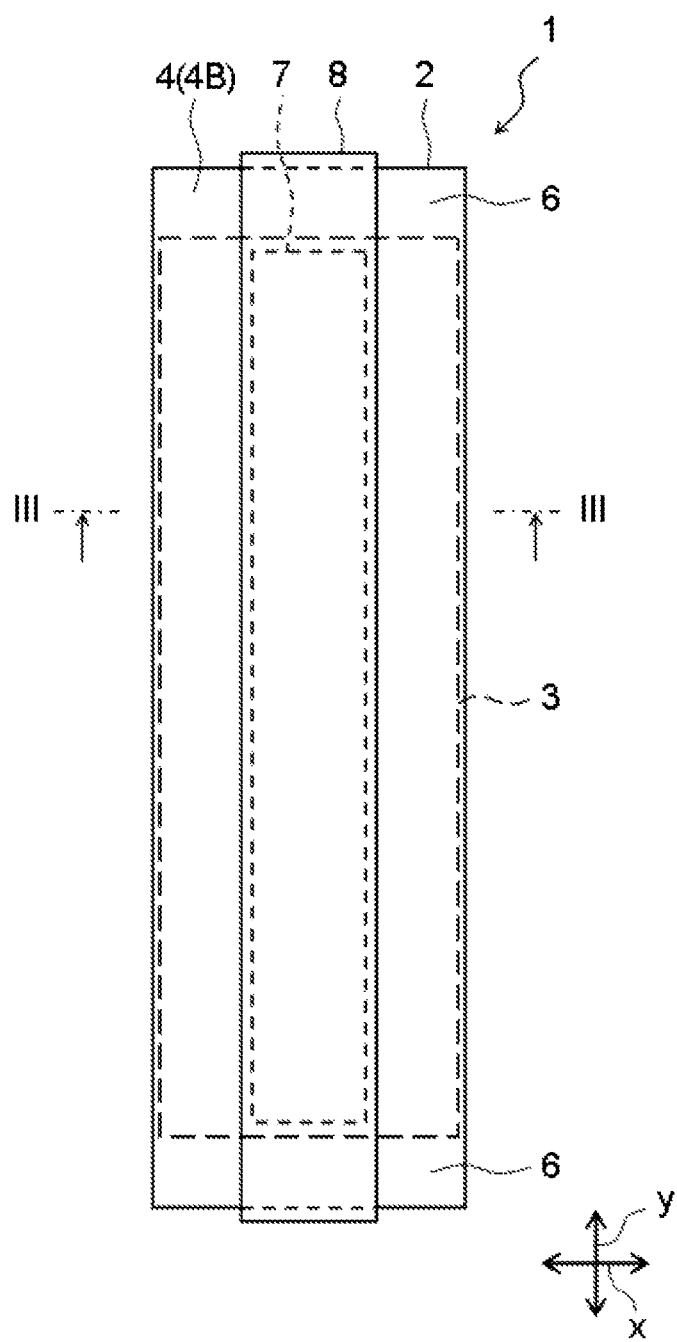

[Fig. 3]
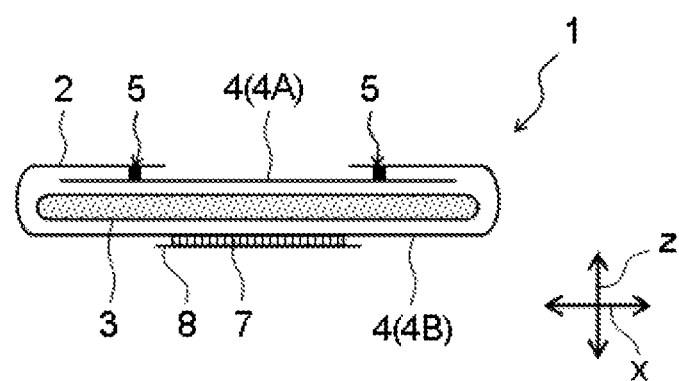

[Fig. 4]
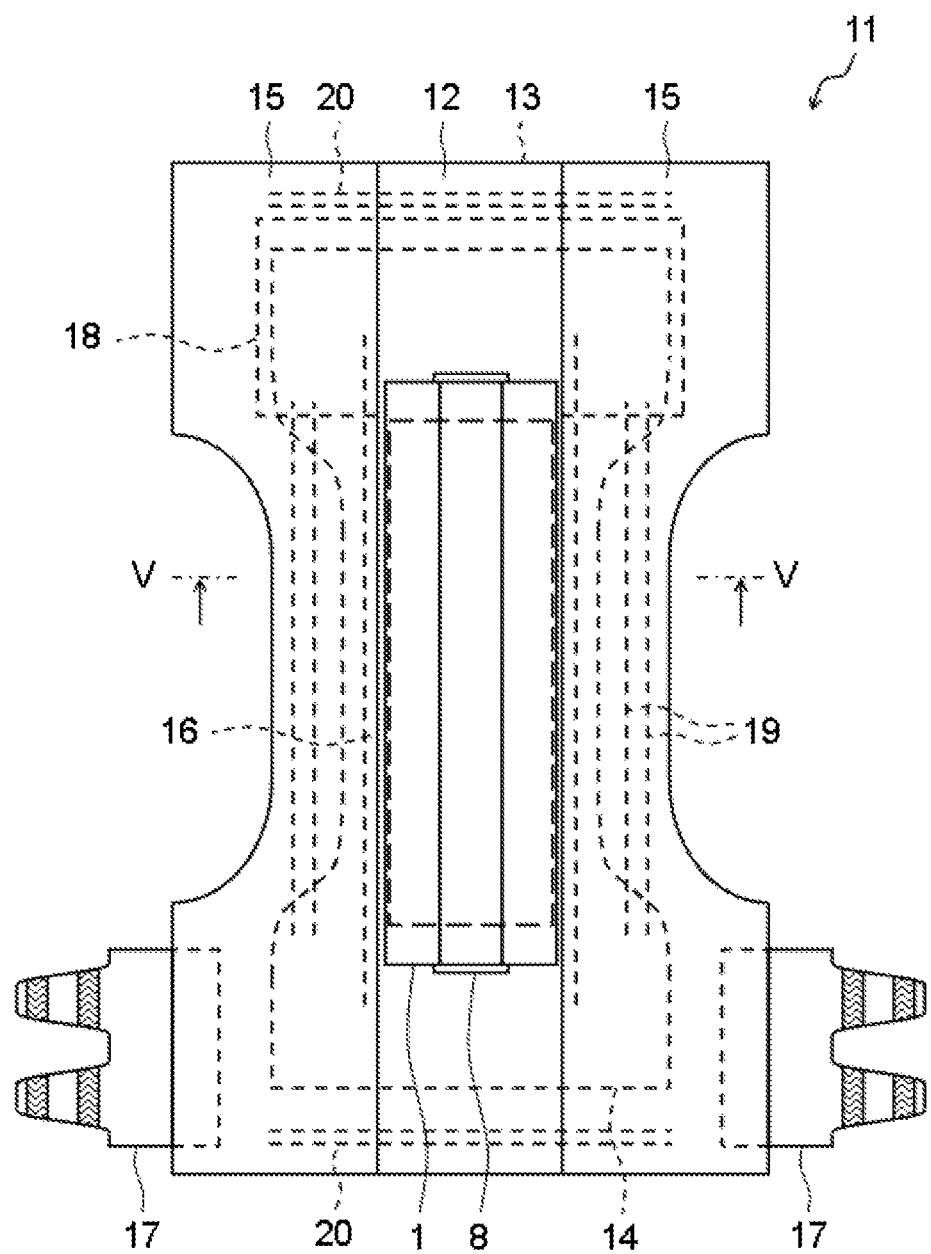

[Fig. 5]
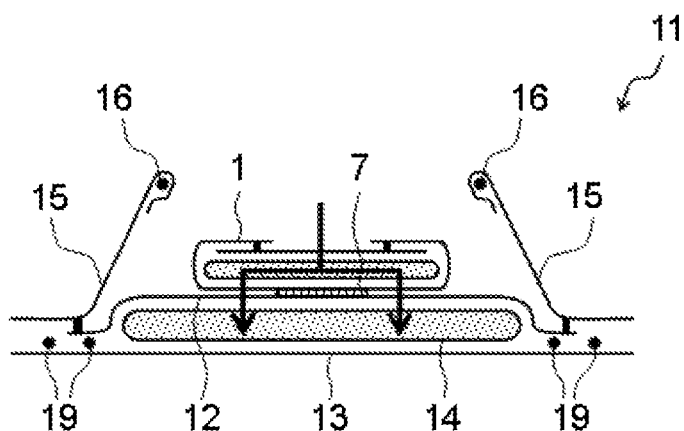

AUXILIARY ABSORBENT ARTICLE

CROSS-REFERENCE TO RELATED APPLICATION

This application claims priority to Japanese Patent Application No. 2019-115623, filed on Jun. 21, 2019, all of the contents of which are incorporated by reference herein.

TECHNICAL FIELD

The present invention relates to an auxiliary absorbent article used in combination with an absorbent article such as a urine pad and a disposable diaper.

BACKGROUND ART

Conventionally, auxiliary absorbent articles used by being attached to a skin surface side of an absorbent article for increasing absorption capacity of the absorbent article or improving leakage prevention effects are known (for example, Japanese Unexamined Application Publication No. H11-267145, Japanese Unexamined Application Publication No. 2004-261442, and Japanese Unexamined Application Publication No. 2011-72612).

SUMMARY OF INVENTION

Technical Problem

An auxiliary absorbent article may be provided with an adhesive part on its outer facing side for attaching to a skin facing side of an absorbent article, and the adhesive part is generally covered with a release sheet before using the auxiliary absorbent article. The thus constituted auxiliary absorbent article is desired to be attached to a desired position of the absorbent article properly when using it, and thereby, urine or the like excreted from a wearer can be absorbed by the auxiliary absorbent article, that enhances absorption capacity and leakage prevention effect.

The present invention has been made in view of the above circumstances, and an object of the present invention is to provide an auxiliary absorbent article that is used by attaching to a skin facing side of an absorbent article and can be easily attached to a desired position of the absorbent article when using it.

Solution to Problem

The auxiliary absorbent article of the present invention which solves the above problems is an auxiliary absorbent article that is used by attaching to a skin facing side of an absorbent article and has a longitudinal direction and a width direction, comprising: a main body comprising an absorber and a liquid-permeable cover sheet which covers a skin facing side and an outer facing side of the absorber; an adhesive part provided on an outer facing side of the main body; and a release sheet provided on an outer facing side of the adhesive part so as to cover the adhesive part; wherein the release sheet extends in the longitudinal direction and extends outward in the longitudinal direction beyond at least one end edge in the longitudinal direction of the main body.

In the auxiliary absorbent article of the present invention, the release sheet covering the adhesive part is provided so as to extend outward in the longitudinal direction beyond at least one end edge in the longitudinal direction of the main body as described above. Therefore, after placing the auxiliary absorbent article on a skin facing side of an absorbent article to determine an approximate mounting position, the release sheet is peeled off by pinching or hooking a longitudinal end of the release sheet with a finger in that state, whereby it becomes easy to attach the auxiliary absorbent article to a desired position properly without moving the position of the auxiliary absorbent article significantly.

It is preferable that the release sheet extends outward in the longitudinal direction beyond both end edges in the longitudinal direction of the main body. Thereby, the release sheet can be easily peeled off from both one side and the other side in the longitudinal direction of the auxiliary absorbent article, that facilitates the attaching of the auxiliary absorbent article.

It is preferable that the cover sheet includes a first cover sheet provided on the skin facing side of the absorber and a second cover sheet provided on the outer facing side of the absorber, and both end parts in the width direction of the second cover sheet are folded back along lateral edges in the width direction of the absorber and joined to a skin facing side of the first cover sheet. By constituting the cover sheet in this manner, a portion where the cover sheet extends outward in the width direction from the absorber is not formed on both ends in the width direction of the auxiliary absorbent article, whereby absorption ability of urine or the like from lateral sides in the width direction of the auxiliary absorbent article can be enhanced. Further, when urine or the like is excreted on the first cover sheet from a wearer and diffuses on the first cover sheet in the width direction, the second cover sheet prevents the urine or the like from further diffusing outward in the width direction, and more amount of urine or the like is easily absorbed by the auxiliary absorbent article suitably.

In the case of constituting the cover sheet as described above, it is preferable that joint portions of the second cover sheet with the first cover sheet are formed in a region within 15 mm from both end edges in the width direction of the second cover sheet over an entire longitudinal direction, and both end edges in the width direction of the second cover sheet are not joined to the first cover sheet. In this case, a gap is formed between the first cover sheet and the end edges in the width direction of the second cover sheet, and this gap makes it difficult for urine or the like that has diffused in the width direction on the first cover sheet to flow over the second cover sheet. Therefore, urine or the like is more easily absorbed by the auxiliary absorbent article.

It is preferable that the cover sheet extends outward in the longitudinal direction beyond both end edges in the longitudinal direction of the absorber, whereby margin portions in which the absorber does not exist are formed on both end parts in the longitudinal direction of the main body, and the adhesive part is provided at a position overlapping with the absorber and is not provided in an outer half region that is formed by equally bisecting the margin portion in the longitudinal direction. By providing the adhesive part in this manner, it becomes easy to pinch or hook the longitudinal end of the release sheet with a finger, and the peeling of the release sheet is facilitated.

It is preferable that the adhesive part is provided so as to overlap with a center line in the width direction of the main body and extend in the longitudinal direction. As the adhesive part is provided in this manner, the adhesive part provided at a center part in the width direction of the main body functions as an impermeable layer when urine or the like excreted from a wearer is absorbed by the auxiliary absorbent article, whereby urine or the like is less likely to quickly permeate in the thickness direction of the auxiliary absorbent article and easily diffuses in the width direction or the longitudinal direction inside the auxiliary absorbent article. Therefore, more parts of the auxiliary absorbent article are likely to contribute to absorption of urine or the like.

The release sheet is preferably formed narrower in the width direction than the main body. Thereby, when peeling off the release sheet from the main body, the main body can be held by one hand and the release sheet can be pinched by the other hand, and the peeling of the release sheet becomes easy.

The release sheet may be configured that the release sheet includes a first release sheet provided on one side in the longitudinal direction and a second release sheet provided on the other side in the longitudinal direction, the first release sheet extends outward in the longitudinal direction beyond one end edge in the longitudinal direction of the main body, and the second release sheet extends outward in the longitudinal direction beyond the other end edge in the longitudinal direction of the main body. By providing the first release sheet and the second release sheet in this manner, it becomes further easier to appropriately attach the auxiliary absorbent article to a desired position of the absorbent article. That is, after placing the auxiliary absorbent article on a skin facing side of the absorbent article to determine an approximate mounting position, the first release sheet is peeled off while fixing the position of the other side of the auxiliary absorbent article in the longitudinal direction, one side of the absorber in the longitudinal direction is attached to the skin facing side of the absorbent article, the second release sheet is further peeled off, and the other side of the auxiliary absorbent article in the longitudinal direction is attached to the skin facing side of the absorbent article, whereby the auxiliary absorbent article can be easily attached to the desired position properly.

The release sheet may be provided with a cuttable line that separates the release sheet into two in the longitudinal direction. In this case, by cutting the release sheet along the cuttable line, the first release sheet and the second release sheet are formed on one side and the other side in the longitudinal direction, respectively. Therefore, even when the release sheet is formed in this manner, it is easy to attach the auxiliary absorbent article to the desired position properly.

Advantageous Effects of Invention

In the auxiliary absorbent article of the present invention, an adhesive part is provided on the outer facing side and a release sheet covering the adhesive part is provided so as to extend outward in the longitudinal direction beyond at least one end edge in the longitudinal direction of the main body. Therefore, after placing the auxiliary absorbent article on a skin facing side of an absorbent article to determine an approximate mounting position, the release sheet is peeled off by pinching or hooking a longitudinal end of the release sheet with a finger in that state, whereby it becomes easy to attach the auxiliary absorbent article to a desired position properly without moving the position of the auxiliary absorbent article significantly.

BRIEF DESCRIPTION OF THE DRAWINGS

FIG. 1 shows an example of an auxiliary absorbent article of the present invention, and shows a plan view of the absorbent article as viewed from a skin facing side thereof.

FIG. 2 shows a plan view of the absorbent article shown in FIG. 1 as viewed from an outer facing side thereof.

FIG. 3 shows a cross-sectional view taken along a line III-III of the absorbent article shown in FIGS. 1 and 2.

FIG. 4 shows an example of attaching the auxiliary absorbent article of the present invention to an absorbent article, and shows a plan view of the auxiliary absorbent article placed on a skin facing side of the absorbent article as viewed from a skin facing side thereof.

FIG. 5 shows a cross-sectional view taken along a line V-V of the absorbent article to which the auxiliary absorbent article is attached shown in FIG. 4, and represents a state where the auxiliary absorbent article with a release sheet peeled off is attached to a skin facing side of the absorbent article.

DESCRIPTION OF THE PREFERRED EMBODIMENTS

An auxiliary absorbent article of the present invention is used by attaching to an absorbent article, and specifically, is used by attaching to a disposable diaper, a urine pad, or the like. The auxiliary absorbent article of the present invention is used by attaching to a skin facing side of an absorbent article, and is used for contributing prevention of lateral leakage of urine or the like by absorbing urine or the like temporarily excreted in a large amount from a wearer, or for increasing absorption capacity of the absorbent article.

The auxiliary absorbent article has a longitudinal direction and a width direction. The auxiliary absorbent article is usually used so that the longitudinal direction of the auxiliary absorbent article substantially coincides with a front-rear direction of an absorbent article and the longitudinal direction of the auxiliary absorbent article corresponds to a front-rear direction of a wearer's crotch. The width direction of the auxiliary absorbent article means a direction perpendicular to the longitudinal direction on the same plane as the auxiliary absorbent article. Further, a direction perpendicular to a plane formed by the longitudinal direction and the width direction is defined as a thickness direction. The auxiliary absorbent article has a skin facing side and an outer facing side with respect to the thickness direction. The skin facing side means a side facing a wearer's skin when the auxiliary absorbent article is used, and the outer facing side means a side facing away from a wearer when the auxiliary absorbent article is used.

The auxiliary absorbent article has a main body comprising an absorber and a liquid-permeable cover sheet which covers a skin facing side and an outer facing side of the absorber. A shape of the main body is not particularly limited. Examples of the shape of the main body include a substantially rectangular shape, an oval shape, an hourglass shape, a battledore shape and others. In view of ease of manufacturing the auxiliary absorbent article, the main body is preferably formed in a substantially rectangular shape. The main body is preferably formed longer in the longitudinal direction than in the width direction, and for example, the length in the longitudinal direction of the main body is preferably 2.0 times or more, more preferably 2.5 times or more, even more preferably 3.0 times or more, and preferably 5.0 times or less, more preferably 4.5 times or less, even more preferably 4.0 times or less of the length in the width direction of the main body.

The absorber is not particularly limited as long as it contains an absorbent material that is able to absorb excrement such as urine. The absorber may include a shaped product of an absorbent material, which is formed into a certain shape, as an absorbent core, or the absorbent core may be wrapped with a cover sheet such as paper (e.g., tissue paper and thin paper) and a liquid-permeable nonwoven fabric. Examples of the absorbent material include, for example, a hydrophilic fiber such as a cellulose fiber, and an absorbent polymer such as a polyacrylic absorbent polymer, a polyasparaginic absorbent polymer, a cellulosic absorbent polymer and a starch-acrylonitrile absorbent polymer. The absorbent material may include a thermal fusion fiber such as a polyolefin (e.g., polyethylene and polypropylene) fiber, a polyester (e.g., PET) fiber and a polyamide fiber. These thermal fusion fibers may be hydrophilized with a surfactant or the like to increase affinity with urine or the like.

It is preferable that the absorbent material essentially contains hydrophilic fibers in view of increasing absorption speed of urine or the like. Therefore, the absorber preferably comprises an absorbent core formed from an aggregate of hydrophilic fibers (particularly pulp fibers). In addition, in view of enhancing absorption capacity, the absorbent material preferably includes an absorbent polymer. Therefore, it is more preferable that the absorbent core is formed from an aggregate of hydrophilic fibers containing an absorbent polymer. In this case, for example, an aggregate of hydrophilic fibers which is mixed with an absorbent polymer or to which an absorbent polymer is dispersed is preferably used as the absorbent core.

Mass per unit area of the absorber is, for example, preferably 100 $g/m^2$ or more, more preferably 120 $g/m^2$ or more, even more preferably 150 $g/m^2$ or more, and thereby an absorption capacity of the auxiliary absorbent article can be increased. Meanwhile, in view of preventing the auxiliary absorbent article from being excessively bulky, mass per unit area of the absorber is preferably 500 $g/m^2$ or less, more preferably 400 $g/m^2$ or less, and even more preferably 300 $g/m^2$ or less.

The cover sheet is liquid permeable and is provided so as to cover both a skin facing side and an outer facing side of the absorber. Thereby, when the auxiliary absorbent article is attached to a skin facing side of an absorbent article and is used, urine or the like excreted from a wearer can be absorbed from a skin facing side of the auxiliary absorbent article, as well as urine or the like overflowed on the skin facing side of the absorbent article can also be absorbed from an outer facing side of the auxiliary absorbent article. The cover sheet is preferably provided so as to cover the entire skin facing side and outer facing side of the absorber.

As the liquid-permeable cover sheet, a nonwoven fabric made from hydrophilic fibers such as cellulose, rayon and cotton; a nonwoven fabric which is formed from hydrophobic fibers such as polyolefin (e.g., polypropylene and polyethylene), polyester (e.g., PET) and polyamide (e.g., nylon), and in which the hydrophobic fibers are hydrophilized with a surfactant on the surface thereof; or the like can be used, for example. As the nonwoven fabric, a spunbonded nonwoven fabric, a point-bonded nonwoven fabric, an air-through nonwoven fabric, a meltblown nonwoven fabric, an airlaid nonwoven fabric, a spunlace nonwoven fabric, an SMS nonwoven fabric or the like can be used. As the liquid-permeable cover sheet, a woven fabric, a knitted fabric, a plastic film having holes may be also used.

The cover sheet may be composed of one sheet or may be composed of a plurality of sheets. For example, the main body may be formed as follows: the cover sheet is composed of one sheet, a center part in the width direction of the sheet is placed on the outer facing side of the absorber, both end parts in the width direction of the sheet are folded back to the skin facing side of the absorber along lateral edges in the width direction of the absorber so that both end parts are placed on the skin facing side of the absorber, and both end parts folded back to the skin facing side are joined to each other. The main body also may be formed as follows: the cover sheet is composed of one sheet, a center part in the width direction of the sheet is placed on the skin facing side of the absorber, both end parts in the width direction of the sheet are folded back to the outer facing side of the absorber along lateral edges in the width direction of the absorber so that both end parts are placed on the outer facing side of the absorber, and both end parts folded back to the outer facing side are joined to each other. Alternatively, the main body may be formed as follows: the cover sheet is composed of one sheet, the sheet is folded in two and the absorber is disposed therebetween, and peripheral edges of the folded sheet are joined to each other.

In the case where the cover sheet is composed of a plurality of sheets, the cover sheet may include a first cover sheet provided on the skin facing side of the absorber and a second cover sheet provided on the outer facing side of the absorber. It is preferable that both the first cover sheet and the second cover sheet are liquid permeable. In this case, the main body can be formed as follows: the absorber is disposed between the first cover sheet and the second cover sheet, and the peripheral edges of the first cover sheet and the second cover sheet are joined to each other. In addition, the main body may be formed as follows: the absorber is disposed between the first cover sheet and the second cover sheet, and both end parts in the width direction of the first cover sheet are folded back to the outer facing side of the absorber along lateral edges in the width direction of the absorber and joined to the second cover sheet. Alternatively, the main body can also be formed as follows: the absorber is disposed between the first cover sheet and the second cover sheet, and both end parts in the width direction of the second cover sheet are folded back to the skin facing side of the absorber along lateral edges in the width direction of the absorber and joined to the first cover sheet.

It is preferable that the cover sheet is folded back to the skin facing side or the outer facing side along the lateral edges in the width direction of the absorber. As a result, on both ends in the width direction of the auxiliary absorbent article, a portion where the cover sheet extends outward in the width direction from the absorber is not formed, whereby absorption ability of urine or the like from lateral side in the width direction of the auxiliary absorbent article can be enhanced. In addition, when using the auxiliary absorbent article, it becomes easy to attach the auxiliary absorbent article to a skin facing side of an absorbent article, and further, it does not occur that uncomfortable feeling, caused by the edge of the cover sheet, which extends outward from the absorber in the width direction, coming into contact with a wearer's skin, is caused to the wearer.

On the other hand, it is preferable that margin portions in which the cover sheets are joined to each other without an absorber are formed at both end parts in the longitudinal direction of the main body. That is, it is preferable that the cover sheet extends outward in the longitudinal direction beyond both end edges in the longitudinal direction of the absorber, whereby the margin portions in which the absorber does not exist are formed at both end parts in the longitudinal direction of the main body. As a result, when attaching or removing the auxiliary absorbent article to or from a skin facing side of an absorbent article, handling the auxiliary absorbent article is facilitated by grasping the margin portions formed on both end parts in the longitudinal direction of the auxiliary absorbent article. The length, with respect to the longitudinal direction, of the margin portion formed on both end parts in the longitudinal direction of the main body is preferably 10 mm or longer, more preferably 15 mm or longer, and preferably 40 mm or shorter, more preferably 30 mm or shorter.

An adhesive part is provided on an outer facing side of the main body part. By providing the adhesive part, the auxiliary absorbent article can be used by being fixed to an absorbent article. Specifically, the adhesive part is provided on an outer facing side of the cover sheet located on the outer facing side of the absorber.

A release sheet is provided on an outer facing side of the adhesive part so as to cover the adhesive part. The release sheet is provided to be capable of being peeled off from the adhesive part, and when using the auxiliary absorbent article, the adhesive part is exposed by peeling off the release sheet, and the auxiliary absorbent article can be attached to a skin facing side of an absorbent article. The release sheet is provided so as to cover the whole of the adhesive part.

The adhesive part may be formed by a pressure-sensitive adhesive. As the pressure-sensitive adhesive, for example, a rubber-based pressure-sensitive adhesive, an acrylic-based pressure-sensitive adhesive, a silicone-based pressure-sensitive adhesive, or the like can be used. Examples of the rubber-based pressure-sensitive adhesive include, for example, natural rubber, polyisoprene, styrene-butadiene copolymer (SBR), styrene-isoprene-styrene block copolymer (SIS), styrene-butadiene-styrene block copolymer (SBS), styrene-ethylene-butadiene-styrene block copolymer (SEBS), styrene-ethylene-propylene-styrene block copolymer (SEPS) and others. As the pressure-sensitive adhesive, only one kind of them may be used, or two or more kinds of them may be used in combination.

The pressure-sensitive adhesive may contain a tackifier, an antioxidant, a plasticizer, a viscosity modifier, or the like. Conventionally known tackifiers can be used, and for example, dicyclopentadiene resin, C5 or C9 hydrocarbon resin, alicyclic hydrocarbon resin, rosin resin, terpene resin and the like can be used.

The release sheet may be made of, for example, a plastic film, or a laminate having a plastic film (for example, a laminate in which paper, a nonwoven fabric, a woven fabric, a knitted fabric or the like is laminated on a plastic film) may be adopted. In the latter case, the release sheet is configured so that the plastic film serves as a contact surface with the adhesive part. As the release sheet, a base material subjected to a peeling process can also be used. Examples of the peeling process include a method of applying a silicone resin to a base material to form a silicone resin layer (silicone processing). At this time, in order to prevent the silicone resin from soaking into the base material, a sealing layer may be provided between the silicone resin and the base material. The sealing layer is composed from, for example, polyethylene or polyvinyl alcohol. In the case where the base material is subjected to the peeling process, paper is preferably used as the base material in view of ease of manufacture and cost.

The release sheet is provided so as to extend in the longitudinal direction and extend outward in the longitudinal direction beyond at least one end edge in the longitudinal direction of the main body. In the auxiliary absorbent article, since the release sheet is provided in this manner, it becomes easy to attach the auxiliary absorbent article to a desired position of an absorbent article. Concretely, after placing the auxiliary absorbent article on a skin facing side of the absorbent article to determine an approximate mounting position, the release sheet is peeled off by pinching or hooking a longitudinal end of the release sheet with a finger in that state, whereby the auxiliary absorbent article can be appropriately attached to a desired position without moving the position of the auxiliary absorbent article significantly.

It is preferable that the release sheet extends outward in the longitudinal direction beyond both end edges of one side and the other side in the longitudinal direction of the main body. Thereby, the release sheet can be easily peeled off from both one side and the other side in the longitudinal direction of the auxiliary absorbent article, that facilitates the attaching of the auxiliary absorbent article.

The release sheet preferably extends 0.5 mm or longer, more preferably 1.0 mm or longer outward beyond the end edge in the longitudinal direction of the main body. By providing the release sheet in this manner, it becomes easy to pinch or hook the longitudinal end of the release sheet with a finger, and the peeling of the release sheet facilitated. Meanwhile, in view of preventing the release sheet from being unintentionally peeled off before the auxiliary absorbent article is used, the release sheet preferably extends 5.0 mm or shorter, more preferably 4.0 mm or shorter, even more preferably 3.0 mm or shorter outward in the longitudinal direction from the end edge in the longitudinal direction of the main body.

The adhesive part is preferably provided so as to extend continuously or intermittently in the longitudinal direction. By providing the adhesive part in this manner, the release sheet is stably installed on the main body. In the case where the adhesive part is provided intermittently in the longitudinal direction, the length of the intermittent portion in the longitudinal direction is preferably 15 mm or shorter, more preferably 10 mm or shorter, and even more preferably 5 mm or shorter.

It is preferable that the adhesive part is provided at a position overlapping with the absorber, and providing that the absorber is divided into three equal parts in the longitudinal direction, that is, a first portion, a second portion and a third portion from one side in the longitudinal direction, the adhesive part is preferably provided at least at a position overlapping with the first portion and the third portion of the absorber. The adhesive part may or may not be provided at a position overlapping with the second portion of the absorber, and in view of stably attaching the auxiliary absorbent article to a skin facing side of an absorbent article, the adhesive part is preferably also provided at a position overlapping with the second portion.

The adhesive part is preferably provided in a region within 20 mm, more preferably in a region within 15 mm inward in the longitudinal direction from both end edges in the longitudinal direction of the absorber. By providing the adhesive part in this manner, the longitudinal ends of the release sheet do not float excessively from the main body and the release sheet is stably installed on the main body. In addition, the auxiliary absorbent article can be stably attached to a skin facing side of an absorbent article. Of course, the adhesive part may be provided in an inner region of that in the longitudinal direction, and for example, it is preferable that the adhesive part is provided continuously or intermittently so as to extend from a region within 20 mm inward in the longitudinal direction from both end edges in the longitudinal direction of the absorber to the second portion of the absorber.

In the case where the margin portions in which the absorber does not exist are provided at both end parts in the longitudinal direction of the main body, it is preferable that the adhesive part is not provided in an outer half region that is formed by equally bisecting the margin portion in the longitudinal direction (that is, a half area of the margin portion on a longitudinal end side). By providing the adhesive part in this manner, it becomes easy to pinch or hook the longitudinal end of the release sheet with a finger, and the peeling of the release sheet is facilitated.

The length of the adhesive part in the width direction is preferably 60% or shorter, more preferably 50% or shorter of the length of the main body in the width direction. As the adhesive part is provided in this manner, when attaching the auxiliary absorbent article to a skin facing side of an absorbent article, the attaching of the auxiliary absorbent article is easily conducted by holding a portion of the main body other than the adhesive part. Meanwhile, in view of ensuring bonding force of the auxiliary absorbent article to a skin facing side of an absorbent article, the length of the adhesive part in the width direction is preferably 10% or longer, more preferably 20% or longer of the length of the main body in the width direction.

It is preferable that the adhesive part is provided so as to overlap with a center line in the width direction of the main body and extend in the longitudinal direction. As the adhesive part is provided in this manner, the adhesive part provided at a center part in the width direction of the main body functions as an impermeable layer when urine or the like excreted from a wearer is absorbed by the auxiliary absorbent article, whereby urine or the like is less likely to quickly permeate in the thickness direction of the auxiliary absorbent article and easily diffuses in the width direction or the longitudinal direction inside the auxiliary absorbent article. Therefore, more parts of the auxiliary absorbent article are likely to contribute to absorption of urine or the like.

The release sheet preferably does not extend outward in the width direction beyond end edges in the width direction of the main body, and is preferably formed narrower in the width direction than the main body. As a result, when peeling off the release sheet from the main body, the main body can be held by one hand and the release sheet can be pinched by the other hand, and the peeling of the release sheet becomes easy. The length of the release sheet in the width direction is preferably 70% or shorter, more preferably 60% or shorter of the length of the main body in the width direction.

Only one release sheet may be provided, or two or more release sheets may be provided. For example, two or more release sheets may be provided side by side in the width direction, and in this case, the release sheets provided side by side in the width direction may be arranged apart from each other, may be arranged in contact with each other, or may be arranged so as to partially overlap with each other. In this case, only one adhesive part may be provided so as to extend in the longitudinal direction, or two or more adhesive parts may be provided side by side in the width direction.

Two release sheets can be also provided side by side in the longitudinal direction. In this case, a first release sheet is provided on one side in the longitudinal direction, a second release sheet is provided on the other side in the longitudinal direction, and the first release sheet can be provided so as to extend outward in the longitudinal direction beyond one end edge in the longitudinal direction of the main body and the second release sheet can be provided so as to extend outward in the longitudinal direction beyond the other end edge in the longitudinal direction of the main body. The first release sheet and the second release sheet may be arranged apart from each other in the longitudinal direction, may be arranged in contact with each other, or may be arranged so as to partially overlap with each other. By providing the first release sheet and the second release sheet in this manner, it becomes further easier to attach the auxiliary absorbent article to a desired position of an absorbent article properly. That is, after placing the auxiliary absorbent article on a skin facing side of the absorbent article to determine an approximate mounting position, the first release sheet is peeled off while fixing the position of the other side of the auxiliary absorbent article in the longitudinal direction, one side of the absorber in the longitudinal direction is attached to the skin facing side of the absorbent article, the second release sheet is further peeled off, and the other side of the auxiliary absorbent article in the longitudinal direction is attached to the skin facing side of the absorbent article, whereby the auxiliary absorbent article can be properly attached to the desired position.

The release sheet may be provided with a cuttable line such as a perforation, and may be formed so as to be separated into two in the longitudinal direction by cutting with the cuttable line. In this case, by cutting the release sheet along the cuttable line, the first release sheet and the second release sheet are formed on one side and the other side in the longitudinal direction, respectively. The cuttable line may be formed so as to extend straight in the width direction, or may be formed so as to extend obliquely. The cuttable line may be provided in a straight line, or may be provided in a curved shape (for example, in a meandering line). In this case, it is preferable that the adhesive part is not provided at a position overlapping with the cuttable line, whereby it becomes easy to cut the release sheet at the cuttable line when pulling the release sheet from one side or the other side in the longitudinal direction.

Next, a configuration example of the auxiliary absorbent article of the present invention is explained with reference to the drawings. FIGS. 1 to 3 show an example of the auxiliary absorbent article of the present invention, FIG. 1 shows a plan view of the auxiliary absorbent article as viewed from a skin facing side thereof, FIG. 2 shows a plan view of the auxiliary absorbent article shown in FIG. 1 as seen from an outer facing side thereof, and FIG. 3 shows a cross-sectional view taken along a line III-III of the auxiliary absorbent article shown in FIGS. 1 and 2. In the drawings, an arrow x represents a width direction, an arrow y represents a longitudinal direction, and an arrow z represents a thickness direction. The present invention is not limited to the embodiments shown in the drawings.

An auxiliary absorbent article 1 comprises a main body 2 in which an absorber 3 is covered with a liquid-permeable cover sheet 4, an adhesive part 7 provided on an outer facing side of the main body 2, and a release sheet 8 provided on an outer facing side of the adhesive part 7 so as to cover the adhesive part 7. The release sheet 8 extends in the longitudinal direction y and extends outward in the longitudinal direction y beyond both end edges in the longitudinal direction y of the main body 2. In the auxiliary absorbent article 1 shown in the drawing, the adhesive part 7 is provided so as to overlap with the absorber 3 and extend in the longitudinal direction y at a center part in the width direction x of the main body 2, and the release sheet 8 is provided so as to cover the adhesive part 7 and extend in the longitudinal direction y at the center part in the width direction x of the main body 2. By providing the release sheet 8 in this manner, the auxiliary absorbent article 1 can be easily attached to a desired position of an absorbent article. This will be explained with reference to FIGS. 4 and 5.

FIGS. 4 and 5 show an example of attaching the auxiliary absorbent article to an absorbent article (a tape-type disposable diaper). FIG. 4 shows a plan view of the auxiliary absorbent article 1 before the release sheet 8 is peeled off, in a state where the auxiliary absorbent article 1 is placed on a skin facing side of a tape-type disposable diaper 11, and FIG. 5 shows a cross-sectional view (that is, V-V cross section in FIG. 4) of the auxiliary absorbent article 1, with the release sheet 8 peeled off, attached to a skin facing side of the absorbent article 11 with the adhesive part 7.

The disposable diaper 11 comprises a top sheet 12, a back sheet 13 and an absorber 14 provided between them. The top sheet 12 is a sheet located on a wearer's side when the absorbent article is worn, and is preferably liquid permeable. As the top sheet 12, a hydrophilic nonwoven fabric, a plastic film having holes, or the like can be used. The back sheet 13 is a sheet located on an opposite side of a wearer, that is, on an outer side when the absorbent article is worn, and is preferably liquid impermeable. As the back sheet 13, a hydrophobic nonwoven fabric, a plastic film, or a laminate of a nonwoven fabric and a plastic film can be used. The absorber 14 is not particularly limited as long as it contains an absorbent material which is capable of absorbing excrement such as urine, and the description of the absorber of the auxiliary absorbent article is referred to.

A pair of side sheets 15 extending in a front-rear direction are provided on both sides in a width direction of the top sheet 12. The side sheet 15 is joined to the top sheet 12, and a rising elastic member 16 is provided at an inner end thereof. In the side sheet 15, the inner end of the side sheet 15 stands up toward a wearer's skin due to contraction force of the rising elastic member 16, thereby forming a rising flap.

The disposable diaper 11 is provided with fastening members 17 on both sides in the width direction of a rear part, and a fastening receiving part 18 is provided on an outer facing side of a front part. The fastening member 17 is configured that an attachment (for example, a hook-and-loop fastener or an adhesive) is provided on a base sheet. The disposable diaper 11 is applied to a crotch of a wearer and the attachment of the fastening member 17 is joined to the fastening receiving part 18, whereby the absorbent article 11 is formed into a pants shape and is worn.

At both end parts in the width direction of the disposable diaper 11, it is preferable that leg elastic members 19 extending in the front-rear direction are provided. The leg elastic member 19 forms gathers around wearer's legs, that improves fit of the disposable diaper 11 around the legs. The disposable diaper 11 is also preferably provided with a waist elastic member 20 extending in the width direction at an end part in the front-rear direction. The waist elastic member 20 forms waist gathers along a waist of a wearer to prevent leakage of urine or the like from an abdominal side or a back side.

As shown in FIG. 4, when attaching the auxiliary absorbent article 1 to a skin facing side of the disposable diaper 11, the auxiliary absorbent article 1 is first placed on the skin facing side of the disposable diaper 11 to determine an approximate mounting position. In the disposable diaper 11 shown in FIG. 4, the auxiliary absorbent article 1 is placed between the rising flaps formed by the left and right side sheets 15. After that, the release sheet 8 is peeled off by pinching or hooking an end of the release sheet 8 is with a finger in that state, and as a result, the auxiliary absorbent article 1 can be appropriately attached to a desired position without moving the position thereof significantly. At this time, since the end of the release sheet 8 is present so as to protrude from the main body 2 of the auxiliary absorbent article 1 in a state where the auxiliary absorbent article 1 is placed on the skin facing side of the disposable diaper 11, pinching the end of the release sheet 8 is facilitated. Further, it becomes easy to arrange the auxiliary absorbent article 1 in a center of the disposable diaper 11 in the width direction with the release sheet 8 as an indicator.

As shown in FIGS. 1 and 2, it is preferable that the cover sheet 4 wrapping the absorber 3 extends outward in the longitudinal direction y beyond both end edges in the longitudinal direction y of the absorber 3, whereby margin portions 6 in which the absorber 3 does not exist are formed on both end parts in the longitudinal direction y of the main body 2. By providing the margin portion 6 in this manner, when attaching or removing the auxiliary absorbent article 1 to or from the skin facing side of the disposable diaper 11, the auxiliary absorbent article 1 can be easily handled by grasping the margin portion 6.

It is preferable that the adhesive part 7 is provided at a position overlapping with the absorber 3 and is not provided in an outer half region formed by equally bisecting the margin portion 6 in the longitudinal direction y. By providing the adhesive part 7 in this manner, it becomes easy to pinch or hook the end in the longitudinal direction y of the release sheet 8 with a finger, and the peeling of the release sheet 8 is facilitated. In FIG. 2, the adhesive part 7 is not provided in the margin portion 6 at all, however, the adhesive part 7 may be provided in an inner half region formed by equally bisecting the margin portion 6 in the longitudinal direction y.

The release sheet 8 is preferably formed narrower in the width direction x than the main body 2. As a result, when peeling off the release sheet 8 from the main body 2, the main body 2 can be held by one hand and the release sheet 8 can be pinched by the other hand, and the peeling of release sheet 8 facilitated.

As shown in FIG. 3, it is preferable that the cover sheet 4 includes a first cover sheet 4A provided on a skin facing side of the absorber 3 and a second cover sheet 4B provided on an outer facing side of the absorber 3, and both end parts in the width direction x of the second cover sheet 4B are folded back along lateral edges in the width direction x of the absorber 3 and joined to the skin facing side of the first cover sheet 4A. By constituting the cover sheet 4 in this manner, a portion where the cover sheet 4 extends outward in the width direction x from the absorber 3 is not formed on both ends in the width direction x of the auxiliary absorbent article 1, whereby absorption ability of urine or the like from lateral sides in the width direction x of the auxiliary absorbent article 1 can be enhanced. Further, when urine or the like is excreted on the first cover sheet 4A from a wearer and diffuses on the first cover sheet 4A in the width direction x, the second cover sheet 4B prevents the urine or the like from further diffusing outward in the width direction x, and urine or the like is easily absorbed by the auxiliary absorbent article 1 suitably.

It is preferable that joint portions 5 of the second cover sheet 4B with the first cover sheet 4A is formed in a region within 15 mm from both end edges in the width direction x of the second cover sheet 4B over the entire longitudinal direction y, and both end edges in the width direction x of the second sheet 4B are not joined to the first cover sheet 4A. That is, it is preferable that both end edges in the width direction x of the second cover sheet 4B are not fixed to the first cover sheet 4A with an adhesive or the like and exist as free ends. In this case, a gap is formed between the first cover sheet 4A and the end edges in the width direction x of the second cover sheet 4B, and this gap makes it difficult for urine or the like that has diffused in the width direction x on the first cover sheet 4A to flow over the second cover sheet 4B. Therefore, urine or the like is more easily absorbed by the auxiliary absorbent article 1. The joint portion 5 is more preferably formed in a region within 12 mm, even more preferably formed in a region within 10 mm from both end edges in the width direction x of the second cover sheet 4. Further, it is preferable that no elastic member is provided on an edge side in the width direction x (that is, an inner side in the width direction x) of the joint portion 5 in the second cover sheet 4B.

The end edge on one side and the end edge on the other side in the width direction x of the second cover sheet 4B folded back on the skin facing side of the absorber 3 are preferably separated from each other by 20 mm or longer, more preferably 25 mm or longer, and even more preferably 30 mm or longer in the width direction x. As a result, an area of the portion where the first cover sheet 4A does not overlap with the second cover sheet 4B on the skin facing side of the absorber 3 is secured, and urine or the like excreted on the first cover sheet 4A is easily absorbed by the auxiliary absorbent article 1 promptly.

The adhesive part 7 is preferably provided so as to overlap with a center line in the width direction x of the auxiliary absorbent article 1 and extend in the longitudinal direction y. When the adhesive part 7 is provided in this manner, urine or the like excreted from a wearer is once absorbed by the auxiliary absorbent article 1 and then diffuses in the width direction x or the longitudinal direction y due to the adhesive part 7 provided in the center part in the width direction x inside the auxiliary absorbent article 1, as shown in FIG. 5, whereby more parts of the auxiliary absorbent article 1 comes to contribute to absorption of urine or the like. When urine or the like is further absorbed by the auxiliary absorbent article 1 in this state, the urine or the like moves through a non-existent part of the adhesive part 7 to the disposable diaper 11 located below the auxiliary absorbent article 1, and the urine or the like is absorbed by the absorber 13 of the disposable diaper 11. By using the auxiliary absorbent article 1 together with the disposable diaper 11 in this manner, a large amount of urine or the like can be absorbed at one time.

REFERENCE SIGNS LIST

1: an auxiliary absorbent article
2: a main body
3: an absorber
4: a cover sheet, 4A: a first cover sheet, 4B: a second cover sheet
5: a joint portion
6: a margin portion
7: an adhesive part
8: a release sheet
11: a disposable diaper (an absorbent article)

The invention claimed is:

1. An auxiliary absorbent article for attachment to a skin facing side of another absorbent article, the auxiliary absorbent article having a longitudinal direction and a width direction, and the auxiliary absorbent article comprising:
a main body including an absorber, a first cover sheet which covers an inner facing side of the absorber and a second cover sheet which covers an outer facing side of the absorber;
an adhesive part on an outer facing side of the main body; and
a release sheet on an outer facing side of the adhesive part to cover the adhesive part,
wherein:
the first cover sheet is liquid-permeable;
the second cover sheet is liquid-permeable;
end parts of the second cover sheet in the width direction are folded back along lateral edges of the absorber in the width direction and joined to an inner facing side of the first cover sheet;
joint portions of the second cover sheet with the first cover sheet are: (i) at a position overlapping with the absorber in a plan view of the auxiliary absorbent article; and (ii) in a region within 15 mm from end edges of the second cover sheet in the width direction over an entire length of the main body in the longitudinal direction;
the end edges of the second cover sheet in the width direction are not joined to the first cover sheet; and
the release sheet extends outward in the longitudinal direction beyond an end edge of the main body.

2. The auxiliary absorbent article according to claim 1, wherein:
the end edge of the main body of the main body is a first end edge of the main body; and
the release sheet extends outward in the longitudinal direction beyond a second end edge of the main body.

3. The auxiliary absorbent article according to claim 1, wherein:
the first cover sheet or the second cover sheet extends outward in the longitudinal direction beyond end edges of the absorber such that margin portions, in which the absorber is not present, are defined on end parts of the main body in the longitudinal direction; and
the adhesive part is at a position overlapping with the absorber and is not present in an outer half region defined by equally bisecting one of the margin portions in the longitudinal direction.

4. The auxiliary absorbent article according to claim 1, wherein
the adhesive part overlaps with a centerline of the main body in the width direction and extends in the longitudinal direction.

5. The auxiliary absorbent article according to claim 1, wherein
the release sheet is narrower in the width direction than the main body.

6. The auxiliary absorbent article according to claim 1, wherein:
the release sheet includes a first release sheet on a first side in the longitudinal direction and the auxiliary absorbent article a second release sheet on a second side in the longitudinal direction;
the end edge of the main body is a first end edge of the main body;
the first release sheet extends outward in the longitudinal direction beyond the first end edge of the main body; and
the second release sheet extends outward in the longitudinal direction beyond a second end edge of the main body.

7. The auxiliary absorbent article according to claim 1, wherein
the release sheet includes a cuttable line that separates the release sheet into two in the longitudinal direction.

8. The auxiliary absorbent article according to claim 1, wherein
the first cover sheet is narrower in the width direction than the absorber.

9. The auxiliary absorbent article according to claim 1, wherein:
- the first cover sheet and the second cover sheet extend outward in the longitudinal direction beyond end edges of the absorber such that margin portions, in which the absorber is not present, are defined on end parts of the main body in the longitudinal direction; and
- the adhesive part is at a position overlapping with the absorber and is not present in an outer half region defined by equally bisecting one of the margin portions in the longitudinal direction.

* * * * *